US011332540B2

United States Patent
Zhang

(10) Patent No.: US 11,332,540 B2
(45) Date of Patent: May 17, 2022

(54) USE OF CIRC-CDH1 INHIBITORS

(71) Applicant: THE FIRST AFFILIATED HOSPITAL, SUN YAT-SEN UNIVERSITY, Guangdong (CN)

(72) Inventor: Nu Zhang, Guangdong (CN)

(73) Assignee: THE FIRST AFFILIATED HOSPITAL, SUN YAT-SEN UNIVERSITY, Guangdong (CN)

( * ) Notice: Subject to any disclaimer, the term of this patent is extended or adjusted under 35 U.S.C. 154(b) by 0 days.

(21) Appl. No.: 16/745,584

(22) Filed: Jan. 17, 2020

(65) Prior Publication Data
US 2020/0231695 A1    Jul. 23, 2020

(30) Foreign Application Priority Data

Jan. 18, 2019  (CN) .......................... 201910048985.8

(51) Int. Cl.
*A61P 35/00* (2006.01)
*C12N 15/113* (2010.01)
*C07K 16/28* (2006.01)

(52) U.S. Cl.
CPC .......... *C07K 16/2896* (2013.01); *A61P 35/00* (2018.01); *C12N 15/113* (2013.01); *C12N 2310/14* (2013.01)

(58) Field of Classification Search
CPC .............. A61P 35/00; C12N 2310/113; C07K 16/2896
See application file for complete search history.

(56) References Cited

PUBLICATIONS

Gao et al. (Nature Cell Biology, 2021 vol. 23:278-291).*
Cancer Research Wales, https://cancerresearchwales.co.uk/blog/no-two-cancers-are-the-same, downloaded on Apr. 7, 2021.*

* cited by examiner

*Primary Examiner* — Terra C Gibbs
(74) *Attorney, Agent, or Firm* — Pearne & Gordon LLP

(57) ABSTRACT

The invention belongs to the field of research and development of genetic engineering antibody drugs, in particular, relates to a method for treating a tumor by administering Circ-CDH1. The Circ-CDH1 is a circular RNA Circ-CDH1 nucleic acid molecule or the protein Circ-CDH1-28 KD expressed by the circular RNA Circ-CDH1 nucleic acid molecule. In particular, a monoclonal antibody Anti-Circ-CDH1 is designed against Circ-CDH1-28 KD, which can specifically detect the content of a protein encoded by endogenous circular RNA Circ-CDH1, can remarkably inhibit invasion and metastasis of cells from tumors such as glioma, breast cancer and the like, and has wide application prospects in clinical detection of tumors and invasion and metastasis treatment.

5 Claims, 5 Drawing Sheets
Specification includes a Sequence Listing.

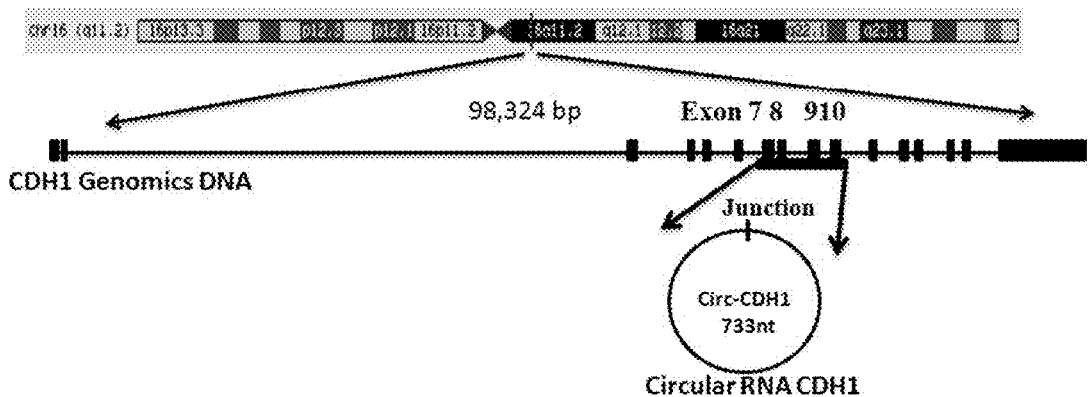

Fig. 1

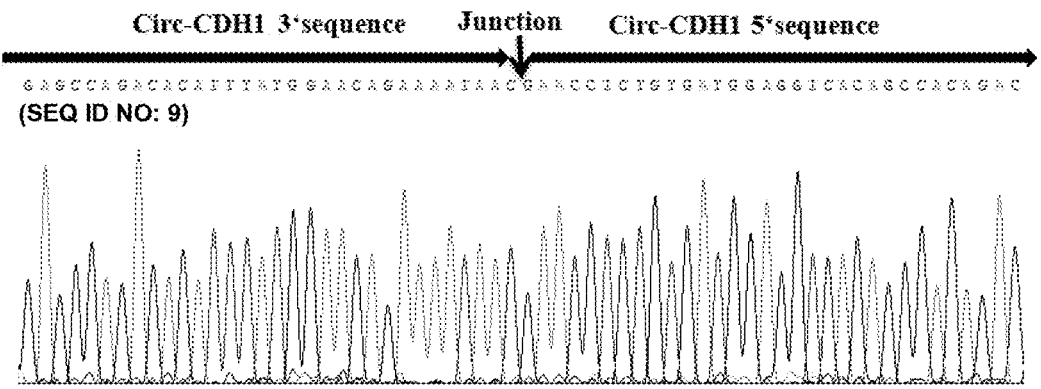

>hsa_circ_0039992|NM_004360|CDH1 733nt
GAACCTCTGTGATGGAGGTCACAGCCACAGACGCGGACGATGATGTGAACACCTACAATGCC
GCCATCGCTTACACCATCCTCAGCCAAGATCCTGAGCTCCCTGACAAAAATATGTTCACCATTA
ACAGGAACACAGGAGTCATCAGTGTGGTCACCACTGGGCTGGACCGAGAGAGTTTCCCTAC
GTATACCCTGGTGGTTCAAGCTGCTGACCTTCAAGGTGAGGGGTTAAGCACAACAGCAACA
GCTGTGATCACAGTCACTGACACCAACGATAATCCTCCGATCTTCAATCCCACCACGTACAAG
GGTCAGGTGCCTGAGAACGAGGCTAACGTCGTAATCACCACACTGAAAGTGACTGATGCTGA
TGCCCCCAATACCCCAGCGTGGGAGGCTGTATACACCATATTGAATGATGATGGTGGACAATT
TGTCGTCACCACAAATCCAGTGAACAACGATGGCATTTTGAAAACAGCAAAGGGCTTGGATT
TTGAGGCCAAGCAGCAGTACATTCTACACGTAGCAGTGACGAATGTGGTACCTTTTGAGGTC
TCTCTCACCACCTCCACAGCCACCGTCACCGTGGATGTGCTGGATGTGAATGAAGCCCCATC
TTTGTGCCTCCTGAAAAGAGAGTGGAAGTGTCCGAGGACTTTGGCGTGGGCCAGGAAATCA
CATCCTACACTGCCCAGGAGCCAGACACATTTATGGAACAGAAAATAAC (SEQ ID NO: 1)

Fig. 2

Circ-CDH1-28KD 254aa
MEVTATDADDDVNTYNAAIAYTILSQDPELPDKNMFTI
NRNTGVISVVTTGLDRESFPTYTLVVQAADLQGEGLST
TATAVITVTDTNDNPPIFNPTTYKGQVPENEANVVITTL
KVTDADAPNTPAWEAVYTILNDDGGQFVVTTNPVNN
DGILKTAKGLDFEAKQQYILHVAVTNVVPFEVSLTTSTA
TVTVDVLDVNEAPIFVPPEKRVEVSEDFGVGQEITSYT
AQEPDTFMEQKI*TNLCDGGHSHRRGR* (SEQ ID NO: 2)
               Antibody Binding

SEQUENCE LISTING

<160> NUMBER OF SEQ ID NOS: 10

<210> SEQ ID NO 1
<211> LENGTH: 733
<212> TYPE: DNA
<213> ORGANISM: Homo sapiens
<220> FEATURE:
<221> NAME/KEY: misc_feature
<222> LOCATION: (1)..(733)
<223> OTHER INFORMATION: Circ-CDH1-733 circular molecules nucleic acid
      sequence

<400> SEQUENCE: 1
gaacctctgt gatggaggtc acagccacag acgcggacga tgatgtgaac acctacaatg      60
ccgccatcgc ttacaccatc ctcagccaag atcctgagct ccctgacaaa aatatgttca     120
ccattaacag gaacacagga gtcatcagtg tggtcaccac tgggctggac cgagagagtt     180
tccctacgta taccctggtg gttcaagctg ctgaccttca aggtgagggg ttaagcacaa     240
cagcaacagc tgtgatcaca gtcactgaca ccaacgataa tcctccgatc ttcaatccca     300
ccacgtacaa gggtcaggtg cctgagaacg aggctaacgt cgtaatcacc acactgaaag     360
tgactgatgc tgatgccccc aatacccag cgtgggaggc tgtatacacc atattgaatg     420
atgatggtgg acaatttgtc gtcaccacaa atccagtgaa caacgatggc attttgaaaa     480
cagcaaaggg cttggatttt gaggccaagc agcagtacat tctacacgta gcagtgacga     540
atgtggtacc ttttgaggtc tctctcacca cctccacagc caccgtcacc gtggatgtgc     600
tggatgtgaa tgaagcccc atctttgtgc ctcctgaaaa gagagtggaa gtgtccgagg     660
actttggcgt gggccaggaa atcacatcct acactgccca ggagccagac acatttatgg     720
aacagaaaat aac                                                        733

<210> SEQ ID NO 2
<211> LENGTH: 254
<212> TYPE: PRT
<213> ORGANISM: Homo sapiens
<220> FEATURE:
<221> NAME/KEY: MISC_FEATURE
<222> LOCATION: (1)..(254)
<223> OTHER INFORMATION: Circ-CDH1-28 amino acid sequence

<400> SEQUENCE: 2

Met Glu Val Thr Ala Thr Asp Ala Asp Asp Val Asn Thr Tyr Asn
1               5                   10                  15

Ala Ala Ile Ala Tyr Thr Ile Leu Ser Gln Asp Pro Glu Leu Pro Asp
                20                  25                  30

Lys Asn Met Phe Thr Ile Asn Arg Asn Thr Gly Val Ile Ser Val Val
        35                  40                  45

Thr Thr Gly Leu Asp Arg Glu Ser Phe Pro Thr Tyr Thr Leu Val Val
    50                  55                  60

Gln Ala Ala Asp Leu Gln Gly Glu Gly Leu Ser Thr Thr Ala Thr Ala
65                  70                  75                  80

Val Ile Thr Val Thr Asp Thr Asn Asp Asn Pro Pro Ile Phe Asn Pro
                85                  90                  95

Thr Thr Tyr Lys Gly Gln Val Pro Glu Asn Glu Ala Asn Val Val Ile
                100                 105                 110

Thr Thr Leu Lys Val Thr Asp Ala Asp Ala Pro Asn Thr Pro Ala Trp
            115                 120                 125

Glu Ala Val Tyr Thr Ile Leu Asn Asp Asp Gly Gly Gln Phe Val Val
        130                 135                 140

```
Thr Thr Asn Pro Val Asn Asn Asp Gly Ile Leu Lys Thr Ala Lys Gly
145                 150                 155                 160

Leu Asp Phe Glu Ala Lys Gln Gln Tyr Ile Leu His Val Ala Val Thr
                165                 170                 175

Asn Val Val Pro Phe Glu Val Ser Leu Thr Thr Ser Thr Ala Thr Val
            180                 185                 190

Thr Val Asp Val Leu Asp Val Asn Glu Ala Pro Ile Phe Val Pro Pro
        195                 200                 205

Glu Lys Arg Val Glu Val Ser Glu Asp Phe Gly Val Gly Gln Glu Ile
    210                 215                 220

Thr Ser Tyr Thr Ala Gln Glu Pro Asp Thr Phe Met Glu Gln Lys Ile
225                 230                 235                 240

Thr Asn Leu Cys Asp Gly Gly His Ser His Arg Arg Gly Arg
                245                 250
```

<210> SEQ ID NO 3
<211> LENGTH: 11
<212> TYPE: PRT
<213> ORGANISM: Artificial sequence
<220> FEATURE:
<223> OTHER INFORMATION: Synthetic construct immunogen

<400> SEQUENCE: 3

```
Cys Asp Gly Gly His Ser His Arg Arg Gly Arg
1               5                   10
```

<210> SEQ ID NO 4
<211> LENGTH: 20
<212> TYPE: DNA
<213> ORGANISM: Artificial sequence
<220> FEATURE:
<223> OTHER INFORMATION: Synthetic construct primer F of interface
      sequence

<400> SEQUENCE: 4
gtgggccagg aaatcacatc                                              20

<210> SEQ ID NO 5
<211> LENGTH: 20
<212> TYPE: DNA
<213> ORGANISM: Artificial sequence
<220> FEATURE:
<223> OTHER INFORMATION: Synthetic construct primer R of interface
      sequence

<400> SEQUENCE: 5
tcacatcatc gtccgcgtct                                              20

<210> SEQ ID NO 6
<211> LENGTH: 23
<212> TYPE: DNA
<213> ORGANISM: Artificial sequence
<220> FEATURE:
<223> OTHER INFORMATION: Synthetic construct si-RNA1

<400> SEQUENCE: 6
aacagaaaau aacgaaccuc utt                                          23

<210> SEQ ID NO 7
<211> LENGTH: 23
<212> TYPE: DNA
<213> ORGANISM: Artificial sequence
<220> FEATURE:

```
<223> OTHER INFORMATION: Synthetic construct si-RNA2

<400> SEQUENCE: 7
auaacgaacc ucugugaugg att                                              23

<210> SEQ ID NO 8
<211> LENGTH: 23
<212> TYPE: DNA
<213> ORGANISM: Artificial sequence
<220> FEATURE:
<223> OTHER INFORMATION: Synthetic construct si-RNA3

<400> SEQUENCE: 8
aauaacgaac cucugugaug gtt                                              23

<210> SEQ ID NO 9
<211> LENGTH: 64
<212> TYPE: DNA
<213> ORGANISM: Homo sapiens
<220> FEATURE:
<221> NAME/KEY: misc_feature
<222> LOCATION: (1)..(64)
<223> OTHER INFORMATION: interface sequence

<400> SEQUENCE: 9
gagccagaca catttatgga acagaaaata acgaacctct gtgatggagg tcacagccac      60
agac                                                                   64

<210> SEQ ID NO 10
<211> LENGTH: 200
<212> TYPE: DNA
<213> ORGANISM: Homo sapiens
<220> FEATURE:
<221> NAME/KEY: misc_feature
<222> LOCATION: (1)..(200)
<223> OTHER INFORMATION: interface sequence

<400> SEQUENCE: 10
ctgaaaagag agtggaagtg tccgaggact ttggcgtggg ccaggaaatc acatcctaca      60
ctgcccagga gccagacaca tttatggaac agaaaataac gaacctctgt gatggaggtc     120
acagccacag acgcggacga tgatgtgaac acctacaatg ccgccatcgc ttacaccatc     180
ctcagccaag atcctgagct                                                 200
```

USE OF CIRC-CDH1 INHIBITORS

CROSS-REFERENCE TO RELATED APPLICATIONS

This application claims priority to Chinese Patent Application 201910048985.8, filed Jan. 18, 2019, which is hereby incorporated by reference.

BACKGROUND OF THE INVENTION

Technical Field

The invention belongs to the field of research and development of genetic engineering antibody drugs, and relates to a use of a Circ-CDH1 inhibitor.

Background Art

Since 2012, a large number of circular RNAs (circular RNA, circRNA) have been found in organisms, which are a kind of RNA with special functions and exist in large quantities objectively. Circular RNA is formed by splicing a precursor RNA, followed by head-to-tail ligation of a linear RNA. Previous studies have not found the objective existence of this circular RNA due to the limitations of technical level. With the development of deep RNA sequencing and large-scale bioinformatics, researchers have found that there are a large number of circular RNA molecules in the organism, which are very stable in the organism as they form the closed loop. There are few studies on the specific functions and molecular mechanisms of circular RNAs, and there are only a few hypotheses: circular RNAs can be used as "sponges" to absorb miRNAs and inhibit the functions of the miRNAs; circRNAs can directly regulate and control other RNAs levels through base complementary pairing; circRNAs can bind to proteins, inhibit protein activity, recruit components of protein complexes, or regulate and control protein activity, and can also serve as templates for translation to guide protein synthesis.

E-cadherin gene (CDH1) is a tumor suppressor gene located on chromosome 16q22.1. The CDH1 gene encodes epithelial cadherin or E-cadherin, which resides in membranes surrounding epithelial cells, which are cells aligned along the body and gastrovascular cavity surface. E-cadherin belongs to the protein family of cadherins and functions to help adjacent cells adhere to each other (cell adhesion) to form normal tissues. E-cadherin is one of the most thoroughly studied cadherins. In addition to its role in cell adhesion, E-cadherin is involved in intracellular chemical signaling, controls cell maturation and movement, and regulates the activity of certain genes. E-cadherin is also a tumor suppressor protein that prevents cells from growing and dividing too quickly or in an uncontrolled manner. A variety of cancers have been found to be associated with loss of function of the gene, such as breast cancer, ovarian cancer, and gastric cancer.

BRIEF SUMMARY OF THE INVENTION

According to the present invention, there is found a CDH1 variant of circularized pattern in the glial cell line U251, which is formed by head-to-tail circularization of exons 7, 8, 9, and 10 of the CDH1 gene, consists of 733 nucleotides and is designated as Circ-CDH1-733 (see FIG. 1); specifically, the sequence of the Circ-CDH1-733 nucleic acid fragment is shown in SEQ ID NO: 1, and its circBase ID name is: hsa_circ_0039992. The exact circularization interface of the circular RNA is identified by Sanger DNA sequencing (see FIG. 2). After forming a circular RNA molecule, CDH1 forms a complete open reading frame that encodes 254 amino acids and has a protein molecular weight of about 28 KD, which is designated as Circ-CDH1-28 KD (see FIG. 3); specifically, the sequence of the Circ-CDH1-28 KD peptide fragments is shown in SEQ ID NO: 2.

In other embodiments, the present disclosure relates to methods for treating diseases. The present disclosure provides, for example, methods for treating tumors, such as CDH1 mutant tumor or glioma. The present disclosure provides, for example, methods of treating tumors through administering Circ-CDH1-733 nucleic acid fragment inhibitor and/or a Circ-CDH1-28 KD peptide fragment inhibitor.

In some embodiments, the present disclosure relates to a glioma treatment system comprising: 1) a Circ-CDH1-733 and/or Circ-CDH1-28 KD detection system; and 2) a medication system. The medication system comprises a Circ-CDH1-733 nucleic acid fragment inhibitor and/or a Circ-CDH1-28 KD peptide fragment inhibitor.

In some embodiments, the invention disclosure relates to a method for research and development of drugs for treating glioma. According to the method, a corresponding inhibitor or gene therapy tool is designed against the Circ-CDH1-733 nucleic acid fragment.

In other embodiments, the invention disclosure relates to another method for research and development of drugs for treating glioma. According to the method, a corresponding Circ-CDH1-28 KD activity inhibitor is designed against Circ-CDH1-28 KD.

In further embodiments, the invention disclosure relates to a Circ-CDH1-733 specific siRNA.

In some embodiments, the invention disclosure relates to s a polypeptide characterized by the sequence shown in SEQ ID NO: 3.

In other embodiments, the invention disclosure relates to an antibody against Circ-CDH1-28 KD, which is prepared using the amino acid sequence shown in SEQ ID NO: 3 as an immunogen.

In further embodiments, the invention disclosure relates to an antibody anti-CDH1-28 has the amino acid sequence that is at least 90%, at least 91%, at least 92%, at least 93%, at least 94%, at least 95%, at least 96%, at least 97%, at least 98%, at least 99%, or 100% identical to the nucleic acid sequence shown in SEQ ID NO: 11.

In some embodiments, the anti-CDH1-28 has the amino acid sequence shown in SEQ ID NO: 11.

In some embodiments, the present invention disclosure relates to a kit for tumor diagnosis and/or prognosis.

In other embodiments, the present invention disclosure relates to a method for tumor diagnosis and/or prognosis.

BRIEF DESCRIPTION OF THE DRAWINGS

FIG. 1 is a schematic diagram of forming a CDH1 circular RNA;

FIG. 2 is sequencing identification results of the CDH1 circular RNA;

DETAILED DESCRIPTION OF THE INVENTION

The invention aims to provide a novel antitumor drug.

It is another object of the present invention to provide a use of a Circ-CDH1-733 nucleic acid fragment inhibitor in the preparation of antitumor drugs.

It is another object of the present invention to provide a use of Circ-CDH1-28 KD peptide fragment inhibitor in the preparation of antitumor drugs.

It is another object of the present invention to provide a use of Circ-CDH1-733 nucleic acid fragments and/or Circ-CDH1-28 KD peptide fragments in cancer screening/diagnosis or prediction.

It is another object of the present invention to provide antibodies against Circ-CDH1-28 KD.

It is another object of the present invention to provide a Circ-CDH1-733 specific siRNA.

It is another object of the present invention to provide a treatment system for glioma.

It is another object of the present invention to provide a method for research and development of drugs for treating glioma.

In some embodiments, the present disclosure relates to method for treating a tumor in a subject in need thereof, comprising administering to the subject a therapeutically effective amount of Circ-CDH1-733 inhibitor.

Furthermore, the Circ-CDH1-733 inhibitor is a Circ-CDH1-733 nucleic acid fragment inhibitor or a Circ-CDH1-28 KD peptide fragment inhibitor.

Figure 3:
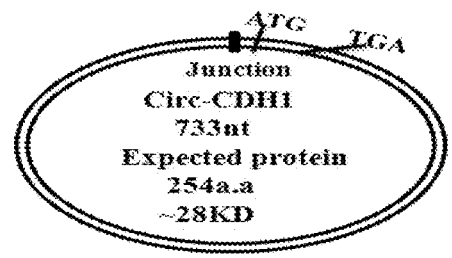
FIG. 3 is a schematic diagram of translating small molecule protein by the CDH1 circular RNA.

Non-obviously, the inventors have identified a CDH1 variant of circularized pattern in the glial cell line U251, which is formed by head-to-tail circularization of exons 7, 8, 9, and 10 of the CDH1 gene and consists of 733 nucleotides and designated as Circ-CDH1-733 (see FIG. 1), specifically, the sequence of the Circ-CDH1-733 nucleic acid fragment has a sequence that is at least 90%, at least 91%, at least 92%, at least 93%, at least 94%, at least 95%, at least 96%, at least 97%, at least 98%, at least 99%, or 100% identical to the nucleic acid sequence shown in SEQ ID NO: 1, and its circBase ID name is: hsa_circ_0039992. The exact circularization interface of the circular RNA is identified by Sanger DNA sequencing (see FIG. 2). After forming a circular RNA molecule, CDH1 forms a complete open reading frame that encodes 254 amino acids and has a protein molecular weight of about 28 KD, which is designated as Circ-CDH1-28 KD (see FIG. 3), specifically, the sequence of the Circ-CDH1-28 KD peptide fragments has a sequence that is at least 90%, at least 91%, at least 92%, at least 93%, at least 94%, at least 95%, at least 96%, at least 97%, at least 98%, at least 99%, or 100% identical to the amino acid sequence is shown in SEQ ID NO: 2.

Although a variety of tumors have been reported to be associated with mutations in the CDH1 gene, the presence of the circular RNA Circ-CDH1-733 and the protein expressed therefrom has never been discovered before. It has not been reported that the gene of Circ-CDH1 is related to glioma. Surprisingly, the inventors have found that the antibody or siRNA can significantly inhibit the growth of tumor cells by preparing specific anti-Circ-CDH1-28 KD monoclonal antibody anti-CDH1-28, or interfering Circ-CDH1-733 with a siRNA, indicating that inhibition of the circular RNA or protein expressed therefrom can inhibit the growth of tumors.

The Circ-CDH1-733 is formed by head-to-tail cyclization of exons 7, 8, 9 and 10 of the CDH1 gene and consists of 733 nucleotides. The CDH1 gene is transcribed in various tumors. In these tumors transcribing the CDH1 gene, it is possible to produce Circ-CDH1-733. In addition to glioma, the inventors have found Circ-CDH1-733 in various tumor types such as breast tumors.

The Circ-CDH1-733 nucleic acid fragment inhibitor is a substance for inhibiting the expression of the entire or local Circ-CDH1-733 nucleic acid fragment.

In some embodiments, the tumor in the invention is glioma.

In some embodiments, the Circ-CDH1-733 nucleic acid fragment inhibitor is a nucleic acid effector molecule. Among patients with glioma, there is an 84.1% probability that Circ-CDH1-733 be detected.

As an alternative embodiment, the nucleic acid effector molecule is DNA, RNA, PNA or a DNA-RNA-hybrid. The nucleic acid effector molecule may be single-stranded or double-stranded. Expression vectors derived from retroviruses, adenoviruses, herpesviruses or vaccinia viruses or from various bacterial plasmids can be used to deliver nucleotide sequences to the targeted organs, tissues or cell population. Such constructs can be used to introduce untranslatable sense or antisense sequences into cells. Even in the absence of integration into DNA, such vectors may continue to transcribe RNA molecules until they are incapacitated by endogenous nucleases.

In some embodiments, the nucleic acid effector molecule may be selected from small inhibitory nucleic acid molecules capable of inhibiting Circ-CDH1-733 expression, such as short interfering RNA (siRNA), double-stranded RNA (dsRNA), microRNA (miRNA), ribozyme, and small hairpin RNA (shRNA), all of which attenuate or eliminate the expression of Circ-CDH1-733 and/or Circ-CDH1-28 KD peptide fragments.

In some embodiments, such small inhibitory nucleic acid molecules may include first and second strands that hybridize to each other to form one or more double-stranded regions, each strand being approximately 18-28 nucleotides in length, approximately 18-23 nucleotides in length, or 18, 19, 20, 21, 22 nucleotides in length. Alternatively, a single strand may comprise regions capable of hybridizing to each other to form a double strand, such as in a shRNA molecule.

In some embodiments, these small inhibitory nucleic acid molecules may include modified nucleotides while maintaining this ability to attenuate or eliminate the expression of Circ-CDH1-733 and/or Circ-CDH1-28 KD peptide fragments. The modified nucleotides can be used to improve in vitro or in vivo properties, such as stability, activity, and/or bioavailability. For example, these modified nucleotides may contain deoxynucleotides, 2'-methyl nucleotides, 2'-deoxy-2'-fluoro nucleotides, 4'-trinucleotides, locked nucleic acids (LNA) nucleotides, and/or 2'-O-methoxyethyl nucleotides, and the like. Small inhibitory nucleic acid molecules, such as short interfering RNA (siRNA), may also contain 5'-and/or 3'-cap structures to prevent degradation by exonucleases.

In some embodiments, a double-stranded nucleic acid composed of small inhibitory nucleic acid molecules contains blunt-ended, or overhanging nucleotides. Other nucleotides may include nucleotides that can cause dislocations, bumps, loops, or wobble base pairs. Small inhibitory nucleic acid molecules can be administrated by formulation, e.g., by liposome encapsulation, or incorporation into other carriers (e.g., biodegradable polymer hydrogels, or cyclodextrins).

Preferably, the Circ-CDH1-733 nucleic acid fragment inhibitor is designed against the nucleic acid sequence of SEQ ID NO: 9.

In some embodiments, the Circ-CDH1-733 nucleic acid fragment inhibitor is a siRNA. As a preferred embodiment, the inhibitor is designed against a Circ-CDH1-733 circular interface; preferably, the inhibitor is designed against any interface-spanning sequence fragment from position 713 to position 20 of Circ-CDH1-733, preferably more than 18 bases in length, which is at least complementary to the sequence from position 716 to position 17 of Circ-CDH1-733; more preferably, the inhibitor is designed against one of the following key fragments of Circ-CDH1-733, or is optionally complementary to the following sequence of Circ-CDH1-733:

a sequence comprising the fragment from position 721 to position 8 of Circ-CDH1-733 or the fragment from position 728 to position 16 of Circ-CDH1-73; preferably, a sequence comprising the fragment from position 727 to position 15 of Circ-CDH1-733. In some preferred embodiments, the sequence is selected from any one of SEQ ID NOs: 6-8.

In some embodiments, the Circ-CDH1-28 KD peptide fragment inhibitor is an antibody or a functional fragment thereof, or a small molecule compound.

As a preferred embodiment, the Circ-CDH1-28 KD peptide fragment inhibitor is an antibody. The antibody may be a monoclonal antibody, a polyclonal antibody, a multivalent antibody, a multispecific antibody (e.g., bispecific antibody), and/or an antibody fragment that specifically binds to a PTEN-31aa molecule. The antibody may be a chimeric antibody, a humanized antibody, a CDR-grafted antibody, or a human antibody, for example. The antibody fragment may be, for example, a Fab, Fab', F(ab')2, Fv, Fd, single chain Fv (scFv), disulfide bond Fv (sdFv), or a VL or a VH domain. The antibody may be in the form of a conjugate, for example, conjugated to a tag, a detectable label, or a cytotoxic agent. The antibody may be of the isotype IgG (e.g., IgG1, IgG2, IgG3 or IgG4), IgA, IgM, IgE or IgD.

In some embodiments, the antibodies may be used with or without modification and may be covalently or non-covalently labeled with, for example, a reporter group or an effector group.

An "antibody fragment" according to the invention exhibits an epitope binding site that is substantially the same as the corresponding antibody and/or has a Circ-CDH1-28 KD peptide fragment inhibitory activity that is substantially the same as that of the corresponding antibody.

The methods for producing antibodies of the invention are known to those skilled in the art.

In some embodiments, the antibody is designed against the amino acid sequence of CDGGHSHRRGR (SEQ ID NO: 3); the antibody is obtained by preparing a monoclonal antibody using the polypeptide CDGGHSHRRGR (SEQ ID NO: 3) as an immunogen.

According to tumor cell scratch assay and cell invasion analysis, it was shown that the antibody anti-CDH1-28 of the present invention can well inhibit the invasion of glioma cells. See FIGS. 5 and 6 for the results.

In some embodiments, the method further comprising, before administering to the subject the therapeutically effective amount of the Circ-CDH1-733 inhibitor, determining that the tumor is a tumor expressing circular Circ-CDH1-733 and translating a corresponding protein.

In some embodiments, the Circ-CDH1-733 inhibitor may be administered once a week, or several times (e.g., 2, 3, 4, 5, 6, 7, 8, 9 or 10) a week. The Circ-CDH1-733 inhibitor may be administered for one or several weeks (1, 2, 3, 4, 5, 6, 7, 8, 9, or 10), for a month, or even for several months (2, 3, 4, 5, 6, 7, 8, 9, 10, 11 or 12 or more). In some instances, treatment may be continued for a year or for several years.

In some embodiments, the Circ-CDH1-733 inhibitor is administered in conjunction with additional anti-tumor therapies. For example, the subject may be further treated with a chemotherapeutic drug (such as an alkylating agent, an anti-metabolite, an anti-mitotic, an alkaloid, a taxane, a topoisomerase inhibitor, a cytotoxic antibiotic, or a combination thereof), radiation, or surgery. In some embodiments, the chemotherapeutic agent is selected from carmustine, fotemustine, lomustine and temozolomide. The subject may also be treated with an antibody therapy, such as bevacizumab and trastuzumab.

In another aspect, the invention disclosure relates to a method for diagnosing and/or prognosing of tumors, comprising detecting the components for Circ-CDH1-733 or/and Circ-CDH1-28 KD.

In yet another aspect, the present invention disclosure relates to a glioma treatment system comprising:
1) a Circ-CDH1-733 and/or Circ-CDH1-28 KD detection system; and
2) a medication system.

The detection system is a detection system capable of detecting circular RNA and peptide fragments expressed by the circular RNA in the prior art, such as fluorescence quantitative PCR instrument and/or immunohistochemistry instrument. The detection system is used to detect the presence of Circ-CDH1-733 and/or Circ-CDH1-28 KD, and if so, the medication system can then be implemented.

The medication system comprises a Circ-CDH1-733 nucleic acid fragment inhibitor and/or a Circ-CDH1-28 KD peptide fragment inhibitor.

Preferably, the Circ-CDH1-733 nucleic acid fragment inhibitor and/or Circ-CDH1-28 KD peptide fragment inhibitor is as described above.

In yet another aspect, the invention disclosure relates to a method for research and development of drugs for treating glioma. According to the method, a corresponding inhibitor or gene therapy tool is designed against the Circ-CDH1-733 nucleic acid fragment; as a preferred embodiment, this is achieved by means of gene interference, gene editing, antisense nucleic acid sequences or locked nucleic acids (LNA).

In yet another aspect, the invention disclosure relates to another method for research and development of drugs for treating glioma. According to the method, a corresponding Circ-CDH1-28 KD activity inhibitor is designed against Circ-CDH1-28 KD. Furthermore, the Circ-CDH1-28K activity inhibitor is an antibody or a functional fragment thereof, or a small molecule compound; preferably, the Circ-CDH1-28 KD activity inhibitor is an antibody.

In yet another aspect, the invention disclosure relates to a Circ-CDH1-733 specific siRNA.

The siRNA is designed against a Circ-CDH1-733 circular interface. Preferably, the siRNA is designed against any interface-spanning sequence fragment from position 713 to position 20 of Circ-CDH1-733; the sequence fragment is preferably more than 18 bases in length and is at least complementary to the sequence from position 716 to position 17 of Circ-CDH1-733.

More preferably, the siRNA is designed against one of the following key fragments of Circ-CDH1-733, or is optionally complementary to the following sequence of Circ-CDH1-733:

a sequence comprising position 721 to position 8 of Circ-CDH1-733; or a sequence comprising position 728 to position 16 of Circ-CDH1-733; or a sequence comprising position 727 to position 15 of Circ-CDH1-733.

As a more preferred embodiment, the siRNA is selected from any one of SEQ ID NOs: 6-8.

In yet another aspect, the invention disclosure relates to a polypeptide characterized by the sequence shown in SEQ ID NO: 3.

In yet another aspect, the invention disclosure relates to a Circ-CDH1-733 nucleic acid fragment having the sequence that is at least 90%, at least 91%, at least 92%, at least 93%, at least 94%, at least 95%, at least 96%, at least 97%, at least 98%, at least 99%, or 100% identical to the nucleic acid sequence shown in SEQ ID NO: 1 or a Circ-CDH1-28 KD peptide fragment having the sequence that is at least 90%, at least 91%, at least 92%, at least 93%, at least 94%, at least 95%, at least 96%, at least 97%, at least 98%, at least 99%, or 100% identical to the amino acid sequence shown in SEQ ID NO: 2.

In some embodiments, the Circ-CDH1-733 nucleic acid fragment is a nucleic acid that has the sequence of SEQ ID NO: 1 except that it contains at least one substitution, addition, and/or deletion modification. It may contain, for example, at least 1, at least 2, at least 3, at least 4, at least 5, at least 10, at least 15, at least 25, or at least 50, substitution, addition, and/or deletion modifications.

In some embodiments, the Circ-CDH1-733 nucleic acid fragment consists of, or consists essentially of, the sequence of SEQ ID NO: 1.

In yet another aspect, the invention disclosure relates to an antibody against Circ-CDH1-28 KD, which is prepared using the amino acid sequence shown in SEQ ID NO: 3 as an immunogen. The antibody may be a monoclonal antibody or a polyclonal antibody. As a preferred embodiment, the antibody is a monoclonal antibody. In one embodiment of the invention, the antibody is a monoclonal antibody prepared against CDGGHSHRRGR (SEQ ID NO: 3) as an immunogen and designated as anti-CDH1-28.

In yet another aspect, the invention disclosure relates to a pharmaceutical composition comprising an antibody as described above. As a preferred embodiment, the pharmaceutical composition comprises antibody anti-CDH1-28. Of course, as a preferred embodiment, the pharmaceutical composition further comprises a pharmaceutically acceptable carrier.

The pharmaceutical composition can be administered to a patient by a variety of routes such as orally, transdermally, subcutaneously, intranasally, intravenously, intramuscularly, intrathecally, topically or locally. Typically, the pharmaceutical compositions will be administered orally, parenterally, intravenously or subcutaneously. According to the administration route, the active components may need to be coated with a material to be protected against the effects of enzymes, acids and other natural conditions that may inactivate the components.

In yet another aspect, the present invention disclosure relates to a kit for tumor diagnosis and/or prognosis, the kit comprising: probes for detecting Circ-CDH1-733, or primers for amplifying Circ-CDH1-733, or antibodies against Circ-CDH1-28 KD protein. As a preferred embodiment of the present invention, the Circ-CDH1-733 detection reagents are directed against the sequence of SEQ ID NO: 10 (near the interface position):

```
                                              SEQ ID NO: 10
CTGAAAAGAGAGTGGAAGTGTCCGAGGACTTTGGCGTGGGCCAGGAAATC

ACATCCTACACTGCCCAGGAGCCAGACACATTTATGGAACAGAAAATAAC

GAACCTCTGTGATGGAGGTCACAGCCACAGACGCGGACGATGATGTGAAC

ACCTACAATGCCGCCATCGCTTACACCATCCTCAGCCAAGATCCTGAGCT
```

In yet another aspect, the present invention disclosure relates to a system for tumor diagnosis and/or prognosis, comprising the following components:

a. detection components for Circ-CDH1-733; and b. results judgment components.

The results judgment components are used for judging the risk of glioma or prognosis according to the expression amount of Circ-CDH1-733 detected by the detection components.

If the expression amount of Circ-CDH1-733 is high, it is judged as high risk; otherwise, it is judged as low risk.

As an implementable manner, the expression level of Circ-CDH1-733 can be divided according to histochemical scores. As a specific histochemical scoring method, the steps are as follows: the results of immunohistochemistry were independently judged by at least two pathologists under double-blind conditions (without knowing any relevant clinical and pathological data).

Judgment of the results: the degree of staining of tissue specimens was observed under an optical microscope. The positive expression of Circ-CDH1-733 protein was mainly characterized by brownish-yellow or brownish-brown granules in the cell membrane and a small amount of brownish-yellow granules in the cytoplasm. Under a high-power microscope (200× amplification), four different visual fields were randomly taken, the total number of cells and the number of nuclear positive cells are counted, and it is scored according to the percentage of the positive cells:

Positive cell rate ≤5%: 1 score;

Positive cell rate >25% and ≤50%: 2 scores;

Positive cell rate >50% and ≤75%: 3 scores;

Positive cell rate >75%: 4 scores;

Meanwhile, it is scored according to the strength and weakness degree of staining:

Negative: 1 score;

Weak staining: 2 scores;

Medium intensity staining: 3 scores;

Strong staining: 4 scores;

The results are judged based on the product of the two: ≤4 scores is (−); >4 and ≤8 is (+); >8 and ≤12 is (+); >12 and ≤16 is (++++). In statistical analysis, (−) and (+) are combined as negative or weak positive expression, (++) and (+++) are combined as strong positive expression. The above results were all determined by at least two pathologists under double-blind conditions.

The expression of the target protein in tumor tissues and normal tissues in immunohistochemical staining results was quantified using an automated measurement program (Carl Zeiss, Oberkochen, Germany) attached to the AxioVision Rel. 4.6 computerized image analysis system: stained immunohistochemistry sections were observed at 200× magnification. Ten representative stained fields were analyzed for each section and the mean optical density (MOD) was calculated and the mean MOD value was used to represent the intensity of staining. The difference of average optical density between different groups was compared by applying t-test, and P≤0.05 indicated statistical significance.

Preferably, the detection components for Circ-CDH1-733 contain Circ-CDH1-733 detection reagents.

Preferably, the detection reagents of Circ-CDH1-733 are probes for detecting Circ-CDH1-733, or primers for amplifying Circ-CDH1-733, or antibodies against Circ-CDH1-28 KD protein.

Preferably, the expression amount of Circ-CDH1-733 is the amount of circular RNA or the amount of protein Circ-CDH1-28 KD expressed by the circular RNA.

Preferably, the Circ-CDH1-733 has the nucleic acid sequence shown in SEQ ID NO: 1.

Preferably, the Circ-CDH1-28 KD has the amino acid sequence shown in SEQ ID NO: 2.

Preferably, the Circ-CDH1-733 detection reagents are directed against the sequence of SEQ ID NO: 10 (near the interface position).

According to the invention, the tumor is a CDH1 mutant tumor type; specifically, the CDH1 mutant tumor is a tumor expressing circular Circ-CDH1-733 and translating corresponding proteins; more specifically, the tumor expressing circular Circ-CDH1-733 and translating the corresponding protein includes, but is not limited to one or more of: glioma, liver cancer, breast cancer, pancreatic cancer, colon cancer, gastric cancer and the like; particularly preferably, the tumor is a glioma.

In some embodiments, there are some beneficial effects: a circularization pattern variant of CDH1, Circ-CDH1-733, and protein Circ-CDH1-28 KD expressed therefrom were found in tumor cells for the first time, and inhibiting of Circ-CDH1-733 or Circ-CDH1-28 KD can achieve tumor inhibition, which provides a new marker for tumor diagnosis and a new target for tumor treatment.

In some embodiments, there are another beneficial effects: the anti-Circ-CDH1-28 KD antibody which designed and synthesized by the invention can effectively inhibit the growth of tumor cells.

Terms

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below.

The term "comprises" means "includes." The abbreviation, "e.g." is derived from the Latin exempli gratia, and is used herein to indicate a non-limiting example. Thus, the abbreviation "e.g." is synonymous with the term "for example."

It should be noted that in the present invention, the term "Circ-CDH1-733" refers to a circular RNA Circ-CDH1-733 nucleic acid fragment, and also refers to a peptide fragment Circ-CDH1-28 KD translated by the circular RNA.

Circ-CDH-733 nucleic acid fragment which has been reported publicly in the invention is a closed circular RNA molecule formed by head-to-tail ligation of exons 7 to 10 of the CDH1 gene and has a length of 733 nt. The Circ-CDH1-733 nucleic acid fragment expression product is a Circ-CDH1-28 KD peptide fragment. Of course, the possibility which should not be excluded is that other variant forms of Circ-CDH-733 will be subsequently found, implementing a similar mechanism. According to the concept of the invention, targeted inhibition, regulation, detection application and the like of the variant forms are also within the scope of the invention.

The term "Circ-CDH1-733 inhibitor" is a substance or tool that causes, at least in part, disruption of the genetic information pathway of the circular RNA Circ-CDH1-733, either at the protein level (Circ-CDH1-28 KD peptide fragment) or at the nucleic acid level (Circ-CDH1-733 nucleic acid fragment). The inhibitors acting at the protein level may be selected from antibodies and/or small molecule compounds and the like. The inhibitors acting at the nucleic acid level are, for example antisense molecules, RNAi molecules and/or ribozymes.

As used herein, the term "nucleic acid" or "nucleic acid fragment" refers to a polymeric form of nucleotides of at least 10 bases in length. The term includes DNA molecules (e.g., cDNA or genomic or synthetic DNA) and RNA molecules (e.g., mRNA or synthetic RNA molecules), as well as analogs of DNA or RNA containing non-natural nucleotide analogs, non-native internucleotide bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation. And, such "nucleic acid" or "nucleic acid fragment" may comprise modified nucleotides as a percentage of the total number of nucleotides present in the nucleic acid molecule, such as at least about 5%, 10%, 15%, 20%, 25%, 30%, 35%, 40%, 45%, 50%, 55%, 60%, 65%, 70%, 75%, 80%, 85%, 90%, 95% or 100% modified nucleotides).

The terms "polypeptide", "micropeptide" and "short peptide" should be construed as having the same meaning to express an amino acid fragment, encompassing both naturally-occurring and non-naturally-occurring proteins, and fragments, mutants, derivatives and analogs thereof, and may be monomeric or polymeric. The terms as used herein encompasses analogs and mimetics that mimic structural and thus biological function.

In present invention that the nucleotide sequences (e.g. siRNA) is administered either alone or in any combination using standard vectors and/or gene delivery systems, and optionally together with a pharmaceutically acceptable carrier or excipient. Subsequent to administration, said nucleotide or vectors may be stably integrated into the genome of the subject.

Furthermore, it is possible to use a pharmaceutical composition of the invention which comprises polynucleotide of the invention in gene therapy. Suitable gene delivery systems may include liposomes, receptor-mediated delivery systems, naked DNA, and viral vectors such as herpes viruses, retroviruses, adenoviruses, and adeno-associated viruses, among others.

The technical solutions of the present invention are further illustrated by the following specific examples, which are not intended to limit the scope of the present invention. Other non-essential modifications and adaptations made by others according to the inventive concept remain within the scope of the invention.

EXAMPLE 1

CDH1 Circular RNA Formation and DNA Sequencing Identification

According to UCSC (website: genome.ucsc.edu/) online database software analysis, it was found that the CDH1 gene is located in the chr16 (q11.2) region of the long arm of human chromosome 16, with a genome spanning 98324 bp and a variant composed of 16 exons encoding the longest protein of 882 amino acids; according to the CDH1 circular RNA information recorded in the circular RNA authoritative database circBase (website: circrna.org/), it was found that exons 7 to 10 of the CDH1 gene form a closed circular RNA molecule by head-to-tail ligation, with a length of 733 nt, which is designated as Circ-CDH1-733 (see FIG. 1), and contains the sequence shown in SEQ ID NO: 1; by designing PCR amplification primers on both sides of the circular RNA ligation site, the sequences of two wings of the circularization site of the circular RNA were amplified, and the exact circularization site of the Circ-CDH1-733 circular RNA was obtained through a Sanger DNA sequencing method. PCR primer sequences for specific PCR amplification of Circ-CDH1-733 were designed as follows:

```
                                    SEQ ID NO: 4
F1: 5' GTGGGCCAGGAAATCACATC 3',

SEQ ID NO: 5
R1: 5' TCACATCATCGTCCGCGTCT 3'
```

The size of the product amplified by the primers is 106 bp; the reaction system and conditions for PCR amplification of target fragments by taking the cDNA of glioma U251 cells 3 as a template are described as follows: PCR system was a total of 30 μL specifically containing 15 μL of 2×PCR MIX (Vazyme), 1.5 μL each of upstream and downstream primers (10 mM), and 1 μL of cDNA template, and 30 μL system was supplemented with sterile water. The reaction conditions were as follows: pre-denaturation at 95° C. for 5 min; followed by 40 cycles of denaturation at 95° C. for 15 s, annealing at 60° C. for 30 s, and extension at 72° C. for 25 s; extension at 72° C. for 5 min after PCR reaction cycles, and then storing at 16° C. The PCR products were purified and then sequenced by a Sanger DNA sequencing method. The exact circularization interface of the circular RNA was identified by a Sanger DNA sequencing method (see FIG. 2).

EXAMPLE 2

Predictive Recognition of Small Molecule Proteins Translated by CDH1 Circular RNA and Preparation of Mouse Monoclonal Antibody The nucleotide sequence analysis of the Circ-CDH1-733 circular RNA molecule showed that the RNA can form an open reading frame consisting of ATG-TGA after cyclization, and can be translated into a novel CDH1 small protein consisting of 254 amino acids; the protein was predicted of about 28 KD molecular weight by a protein molecular weight prediction software (website: www.bio-soft.net/sms/prot_mw.html) and was designated as Circ-CDH1-28 KD (see FIG. 3), containing the sequence shown in SEQ ID NO: 2. Based on the composition of the Circ-CDH1-28 KD amino acid sequence, a mouse monoclonal antibody which can be detected by ELISA, western blot and cell function test was designed by the following method: synthesizing a polypeptide CDGGHSHRRGR (SEQ ID NO: 3) amino acid sequence generated specifically against the circular RNA CDH1 as an immunogen by a method of chemically synthesizing the polypeptide; the standardized preparation procedure for monoclonal antibody preparation was as follows:
1. Five mice were immunized for 2-3 times; 2. Serum were collected from 5 mice for ELISA detection; 3. And after the titer was qualified, a fusion experiment was performed; 4. The splenocytes from the mice with the highest serum titer were fused with myeloma cells; 5. The fused cells were treated by limiting dilution and cloned in 96-well plates; 6. hybridoma cells were screened by HAT medium; 7. Antigen positive 1-10 positive cells were detected by immunogen detection and expanded to 48-well plates; 8. Positive clones were picked and expanded, and a small amount of cells were cryopreserved at −80° C.; 9. Positive clones were obtained by ELISA: each clone was treated by limiting dilution culture in a 96-well plate, and positive sub-clones were screened by ELISA; 10. Positive clones were amplified, and a small amount of cells were cryopreserved at −80° C.; 11. And hybridoma cells were selected to prepare ascites, and ascites were purified by protein A, and purified monoclonal antibodies were obtained.

EXAMPLE 3

Cell Culture and Transfection of siRNA

Glioma cells U251 were seeded in 6-well plates with 500,000 cells and transfected after cell adherence 24 h; before transfection, 100 μL of serum-free culture medium DMEM and siRNA were prepared into a mixed solution; 100 μL of serum-free medium DMEM and 5 μL of lipo2000 liposome were uniformly mixed to prepare a liposome mixed solution; the two mixed solutions were mixed in equal proportion, and stood for 20 min at room temperature; transfection was performed according to the instructions of the transfection reagent (Lipofectamine™ 2000 Transfection Reagent, Thermo Fisher Scientific, #11668019); the final volume of the wells in the 6-well plate was 1 mL, the final concentration of siRNA was 100 nM, after transfection 6 h, the medium was changed into 1 mL of normal medium (10% fetal bovine serum plus 90% DMEM medium plus 1% penicillin streptomycin) for cell culture at 37° C. with 5% carbon dioxide.

Wherein the sequences of siRNAs are as follows:

```
siRNA-1
                                    SEQ ID NO: 6
AACAGAAAAUAACGAACCUCUtt siRNA-2
                                    SEQ ID NO: 7
AUAACGAACCUCUGUGAUGGAtt siRNA-3
                                    SEQ ID NO: 8
AAUAACGAACCUCUGUGAUGGtt
```

After siRNA transfection, the content of Cir-CDH1-733 decreased obviously, and the content of protein translated therefrom also obviously decreased. The three siRNAs were all effective, and the effects of siRNA-2 and siRNA-3 were slightly better than that of siRNA-1 (see FIG. 4).

EXAMPLE 4

The Titer of the Prepared Mouse Monoclonal Antibodies was Determined by ELISA The chemically synthesized polypeptide CDGGHSHRRGR (SEQ ID NO: 3) was diluted 1:5,000 as antigen, added into a polystyrene 96-well reaction plate by 100 µL/well, stood at 4° C. overnight; the mouse monoclonal antibody was serially diluted with PBS, then added into the reaction plate, incubated at 37° C. for 2 h, and washed 3 times; the rabbit anti-mouse IgG-HRP was diluted 1:8,000 with a blocking solution, added into the plate by 100 µL/well, incubated at 37° C. for 1 h, washed 5 times, and washed with distilled water 2 times; the freshly prepared substrate solution was added by 100 µL/well, and stood for 20 min at room temperature in the dark; a stop solution was added by 50 µL/well and the absorbance of each well at 450 nm was measured with a microplate reader. Monoclonal antibodies prepared by ELISA testing (see Table 1).

TABLE 1

Monoclonal antibodies prepared by ELISA assay

| | Dilutions were started at 1 mg/ml | Antibody concentration (ng/ml) | Anti-Circ-CDH1 antibody |
|---|---|---|---|
| 1 | 1/1,000 | 1,000 | 3.064 |
| 2 | 1/2,000 | 500 | 2.855 |
| 3 | 1/4,000 | 250 | 2.52 |
| 4 | 1/8,000 | 125 | 2.148 |
| 5 | 1/16,000 | 62.5 | 1.695 |
| 6 | 1/32,000 | 31.25 | 1.192 |
| 7 | 1/64,000 | 15.62 | 0.785 |
| 8 | 1/128,000 | 7.81 | 0.45 |
| 9 | 1/256,000 | 3.9 | 0.28 |
| 10 | 1/512,000 | 1.95 | 0.19 |

EXAMPLE 5

Western Blotting for Protein Assay

Total cellular protein was extracted with a RIPA lysis solution, and the extracted protein was quantified by a BCA protein quantification method; 5% SDS-PAGE concentrated gel and 15% SDS-PAGE separation gel were prepared, and total loaded protein was 15 µg; the protein was electrophoresed at 80 V for 20 min and 150 V for 1 h and transferred to a membrane at 100 V for 2 h, and the membrane was sealed with 5% skimmed milk for 1 h; the Circ-CDH1-28 KD mouse monoclonal antibody (1:2,000) and (β-actin antibody (abcam Art No. ab197345) (1:3,000) were added for incubation at 4° C. overnight; the next day, the mouse secondary antibody (1:10,000) was added for incubation 1 h at room temperature; the membrane was washed 5 times for 5 min each with TBST, and then illuminated, developed and fixed.

Figure 4:
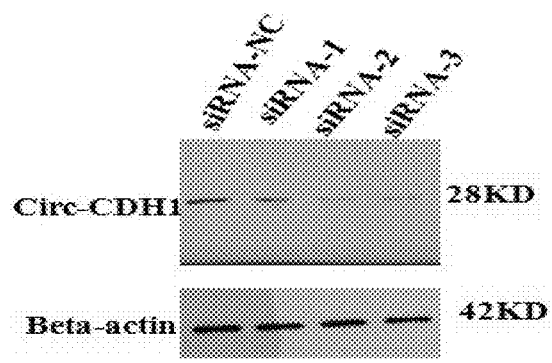
FIG. 4 shows a Western Blotting Assay for detecting the presence of endogenous Circ-CDH1-28 KD protein.

The results are shown in FIG. 4: the expression of Circ-CDH1-28 KD protein in U251 cells was detected by Western Blotting, and the expression of Circ-CDH1-28 KD protein was significantly decreased after interfering with the expression of Circ-CDH1-733 with specific small nucleic acid sequences.

EXAMPLE 6

Wound Healing Assay 500,000 Glioma U251 cells were plated into 6-well plates, and cultured overnight for cells adherence. Cells were scratched the next day, washed 3 times with PBS, and 1 ml of cell culture medium (10% fetal bovine serum plus 90% DMEM medium plus 1% penicillin streptomycin) was added. The culture mediums were grouped based on the Circ-CDH1-28 KD mouse monoclonal antibody concentration of 0 µg/ml, 0.2 µg/ml, 0.4 µg/ml, and 0.8 µg/ml, then cultured at 37° C. with 5% carbon dioxide, and photographed after 24 h.

Figure 5:
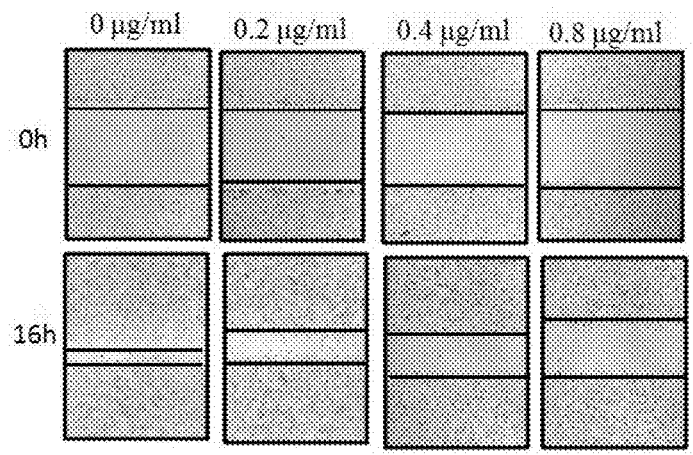
FIG. 5 shows cell scratch assay for detecting antitumor effects of monoclonal antibody anti-CDH1-28.

The experimental results are shown in FIG. 5. After adding monoclonal antibody Circ-CDH1-28 KD, the migration ability of U251 cells decreased obviously, and the inhibition effect of monoclonal antibody on the migration ability of U251 cells increased gradually with the increasing of antibody concentration. It is suggested that Circ-CDH1-28 KD may serve as a potential target.

EXAMPLE 7

Cell Invasion Assay

30 µg of Matrigel gel was spread on the upper chamber of a Transwell chamber, and 200,000 glioma U251 cells were added into the Transwell chamber; the culture mediums were grouped based on the Circ-CDH1-28 KD mouse monoclonal antibody concentration of 0 µg/ml, 0.2 µg/ml, 0.4 µg/ml, and 0.8 µg/ml, then cultured at 37° C. with 5% carbon dioxide for 48 h; the filter membrane was fixed with ethanol, stained with PE, and photographed to count the number of cells passing through Matrigel.

Figure 6:
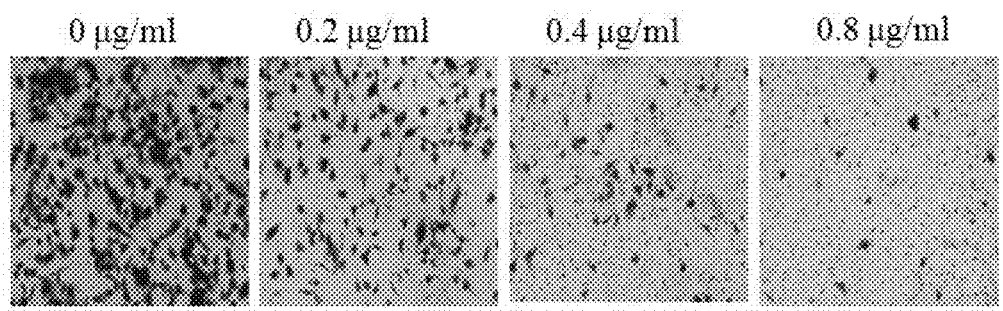
FIG. 6 shows cell invasion analysis experiment for detecting antitumor effects of monoclonal antibody anti-CDH1-28.
Figure 7:
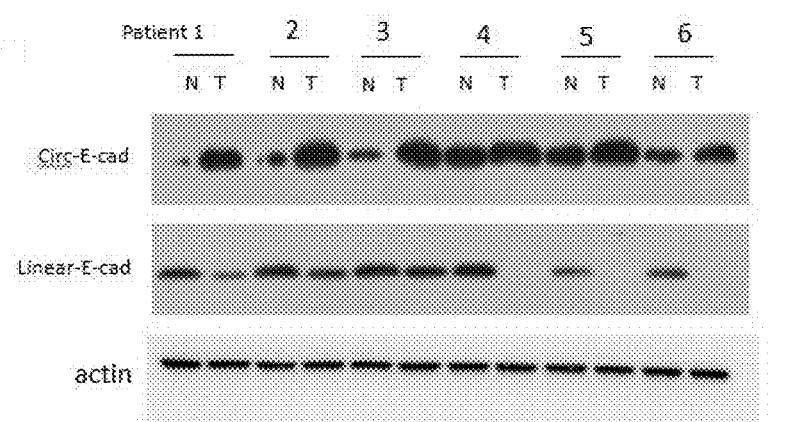
FIG. 7 shows expression of Circ-CDH1-733 in glioma and normal tissues.
Figure 8:
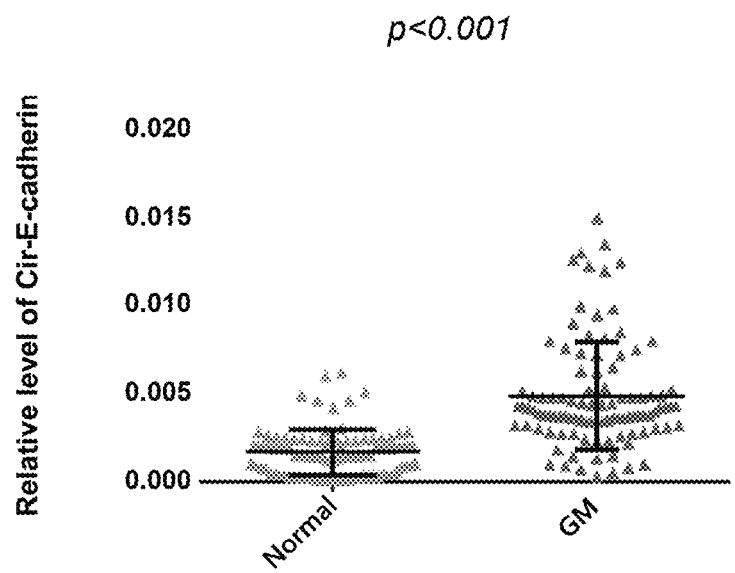
FIG. 8 shows expression of Circ-CDH1-28 KD in glioma and normal tissues.

The results are shown in FIG. 6: after adding monoclonal antibody Circ-CDH1-28 KD, the migration ability of U251 cells decreased obviously, and the inhibition effect of monoclonal antibody on the migration ability of U251 cells increased gradually with the increasing of antibody concentration.

EXAMPLE 8

Figure 9:
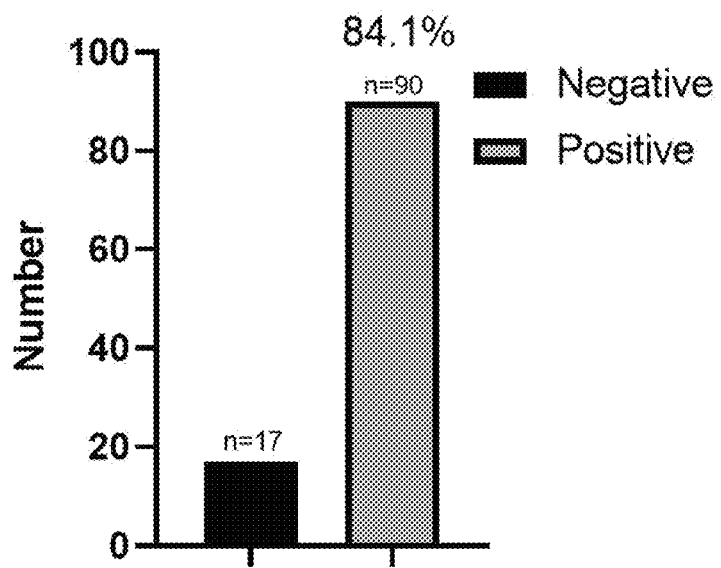
FIG. 9 shows expression paten of Circ-CDH1-28 KD in glioblastoma (GBM) brain tissues.
Figure 10:
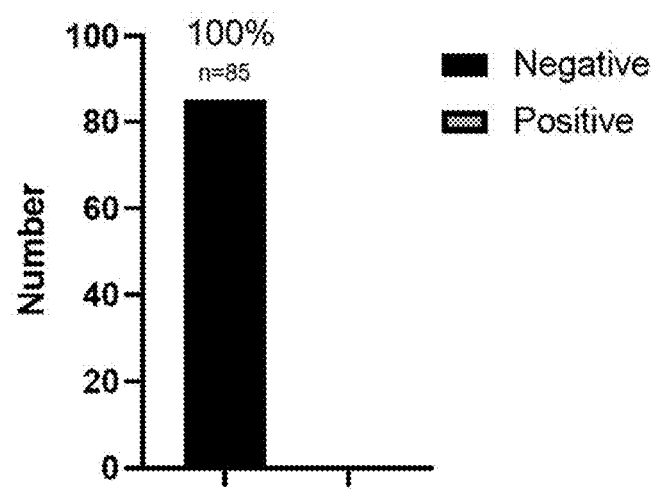
FIG. 10 shows expression paten of Circ-CDH1-28 KD in normal brain tissues.

The Expression Pattern of Circ-CDH1-28 KD in Glioblastoma (GBM) and Normal Brain Tissues Immunohistochemistry (IHC) analysis were performed on a cohort of 107 primary GBM and 85 normal brain tissue specimens. Circ-CDH1-28 KD was undetectable in normal brain tissues. Circ-CDH1-28 KD protein was detected in 90 of 107 GBM samples (84.1%, (see FIG. 9), whereas Circ-CDH1-28 KD was undetectable in all 85 normal brain tissues that were examined (see FIG. 10).

Reference to a "Sequence Listing," a Table, or a Computer Program Listing Appendix Submitted as an ASCII Text File The material in the ASCII text file, named "WANH-62048-Sequences_ST25.txt", created Jan. 15, 2020, file size of 8,192 bytes, is hereby incorporated by reference.

What is claimed is:

1. A method for treating a glioma in a subject in need thereof, comprising administering to the subject a therapeutically effective amount of Circ-CDH1-28KD peptide fragment inhibitor in a form of a monoclonal antibody.

2. The method of claim 1, wherein said glioma is a glioma-tumor expressing circular Circ-CDH1-733 and/or translating a corresponding protein.

3. The method of claim 1, wherein
the Circ-CDH1-28KD peptide fragment has a sequence that is at least 90%, at least 91%, at least 92%, at least 93%, at least 94%, at least 95%, at least 96%, at least 97%, at least 98%, at least 99%, or 100% identical to the amino acid sequence shown in SEQ ID NO: 2.

4. The method of claim 1, wherein said Circ-CDH1-28KD peptide fragment inhibitor is a monoclonal antibody of an immunogen of SEQ ID NO: 3.

5. The method of claim 1, further comprising, before administering to the subject the therapeutically effective amount of the Circ-CDH1-28KD peptide fragment inhibitor, determining that the glioma is a glioma expressing circular Circ-CDHA-733 and translating a corresponding protein.

* * * * *